United States Patent
Akutsu et al.

(10) Patent No.: US 7,130,378 B2
(45) Date of Patent: Oct. 31, 2006

(54) RADIOGRAPHIC X-RAY DEVICE

(75) Inventors: Koji Akutsu, Nara (JP); Mitsuhiro Hashimoto, Ukyo-ku (JP); Mitsuru Umeda, Kamigyo-ku (JP)

(73) Assignee: Shimadzu Corporation, Kyoto (JP)

( * ) Notice: Subject to any disclaimer, the term of this patent is extended or adjusted under 35 U.S.C. 154(b) by 8 days.

(21) Appl. No.: 10/776,595

(22) Filed: Feb. 9, 2004

(65) Prior Publication Data

US 2004/0170255 A1 Sep. 2, 2004

(30) Foreign Application Priority Data

Feb. 27, 2003 (JP) .............................. 2003-050748

(51) Int. Cl.
*H05G 1/26* (2006.01)

(52) U.S. Cl. .................... 378/117; 378/91; 378/92; 378/197

(58) Field of Classification Search ............... 378/91, 378/92, 95, 162, 193, 195–198, 114–117; 600/424, 425, 429, 407; 345/420
See application file for complete search history.

(56) References Cited

U.S. PATENT DOCUMENTS

| | | | | |
|---|---|---|---|---|
| 5,485,502 A | * | 1/1996 | Hinton et al. ............... 378/117 |
| 5,549,439 A | * | 8/1996 | Ploem ........................ 414/680 |
| 5,878,112 A | * | 3/1999 | Koertge ...................... 378/209 |
| 6,272,368 B1 | * | 8/2001 | Alexandrescu .............. 600/407 |
| 6,407,738 B1 | * | 6/2002 | Wakabayashi .............. 345/424 |
| 6,435,713 B1 | * | 8/2002 | Iizuka ........................ 378/195 |
| 6,714,213 B1 | * | 3/2004 | Lithicum et al. ........... 715/701 |
| 6,757,582 B1 | * | 6/2004 | Brisson et al. .............. 700/186 |

* cited by examiner

*Primary Examiner*—Allen C. Ho
(74) *Attorney, Agent, or Firm*—Darby & Darby (57) ABSTRACT

The radiographic X-ray device according to this invention is constituted in such a way that positional relation detecting unit 25 detects in real time the information regarding the positional relations between X-ray imaging systems 4 and 8 that thoroughly represents the overall current status of the positional relations of external surfaces of both X-ray imaging systems 4 and 8 where collisions between first and second X-ray imaging systems 4 and 8 may occur, that the information regarding the positional relations detected by positional relation detecting unit 25 is taken into consideration in controlling the motions of X-ray imaging systems 4 and 8, and that the current status of the positional relations of external surfaces of both X-ray imaging systems 4 and 8 can be thoroughly and accurately reflected upon the motions of X-ray imaging systems 4 and 8 without any difficulty, so that any collisions of X-ray imaging systems 4 and 8 can be avoided without fail.

20 Claims, 6 Drawing Sheets

RADIOGRAPHIC X-RAY DEVICE

INCORPORATION BY REFERENCE

The present application claims priority under 35 U.S.C. §119 to Japanese Patent Application No. 2003-050748 filed on Feb. 27, 2003. The content of that application is incorporated herein by reference.

FIELD OF THE INVENTION

The present invention relates to a radiographic X-ray device equipped with a plurality of X-ray imaging systems each consisting of an X-ray tube for radiating X-rays and an X-ray detector for detecting transmitted X-rays, which are arranged to face each other and are supported on each end of a support arm, an X-ray imaging system transport mechanism, which transports the X-ray imaging systems, in particular to a technology of securely avoiding the X-ray imaging systems from colliding with each other.

BACKGROUND OF THE INVENTION

Figure 6:
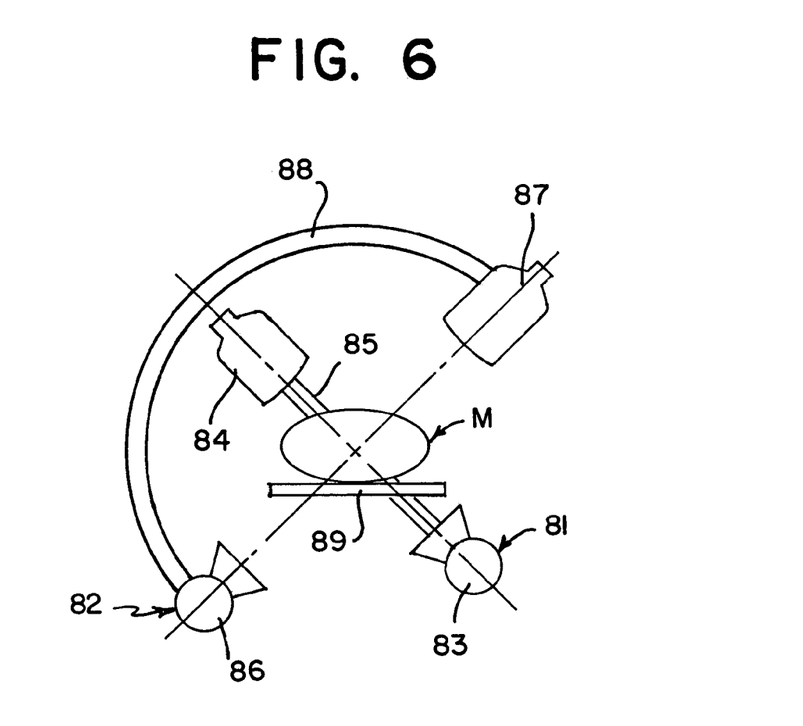
FIG. 6 is a concept drawing showing two sets of X-ray imaging systems used in the conventional radiography of the dual imaging apparatus method.

The radiographic X-ray device based on the double imaging apparatus method, which have hitherto been used typically in healthcare institutions such as hospitals, have had a pair of imaging apparatuses 81 and 82 as shown in FIG. 6. X-ray imaging system 81 comprises an X-ray tube 83 for radiating X-rays and an X-ray detector 84 for detecting transmitted X-rays, which are arranged to face each other and are supported on each end of a C-shaped support arm 85, while X-ray imaging system 82 comprises an X-ray tube 86 for radiating X-rays and an X-ray detector 87 for detecting transmitted X-rays, which are arranged to face each other and are supported on each end of a C-shaped support arm 88, wherein X-ray imaging systems 81 and 82 are moved by rotating and translating C-shaped support arms 85 and 88, thus setting the orientations (shooting directions) and positions (shooting positions) of X-ray imaging systems 81 and 82 respectively to meet the needs of image studies.

Therefore, in the case of the radiographic X-ray device based on the double imaging apparatus method, two X-ray imaging systems 81 and 82 are set up independently in terms of their orientations and positions, thus enabling radiography of a same location of a specimen body M on a top plate 89 from different directions simultaneously by taking X-ray images with X-ray imaging systems 81 and 82 from different directions simultaneously, or radiography of different locations of specimen body M on top plate 89 simultaneously.

The radiographic X-ray device of the prior art based on the double imaging apparatus method, however, has had a problem that X-ray imaging systems 81 and 82 may come in contact with each other while X-ray imaging systems 81 and 82 are in motion. Depending on how the contact occur, damages to X-ray tubes 83 and 86 as well as to X-ray detectors 84 and 87 may occur.

A countermeasure to this concern has been to avoid equipment damages by means of attaching cushioning materials on the areas where contacts are expected to soften the impacts. However, it is difficult to attach cushioning materials to all the places where contacts are expected. Moreover, contact impacts are often be greater than that can be absorbed by cushioning materials.

Another countermeasure has been to have proximity sensors installed at locations of X-ray imaging systems 81 and 82 where contacts may occur so that an alarm can be sounded to call the operator's attention or to stop the motions of X-ray imaging systems 81 and 82 if X-ray imaging systems 81 and 82 come too close to each other. However, it is difficult to install proximity sensors at all locations where contact may occur, so that it is not a secure measure to avoid contacts.

Therefore, the operator has to monitor X-ray imaging systems 81 and 82 visually all the time, and move X-ray imaging systems 81 and 82 at very slow speeds when contacts are likely to occur in order try to avoid contacts. As a result, the picture-taking time tends to be longer, making it an inefficient and painful operation for the operator.

Another possibility is to measure positional relations between X-ray imaging systems 81 and 82 for all possible cases of contacts and register all positional relation data as in a form of a table in order to avoid contacts between X-ray imaging systems 81 and 82 while X-ray imaging systems 81 and 82 are in motion by constantly checking each positional relation data, but the size of the data involved can be enormous if it were to cover all the possible cases of positional relations of X-ray imaging systems 81 and 82 and it is an unrealistic solution in accordance with the work involved in collecting the data and the memory size of data to be registered.

SUMMARY OF THE INVENTION

The present invention is made under such circumstances and is intended to provide a radiographic X-ray device that is capable securely avoiding contacts between the X-ray imaging systems.

The invention has the following constitution in order to achieve the stated purpose.

According to a first implementation of the present invention, a radiographic X-ray device is equipped with a plurality of X-ray imaging systems each consisting of an X-ray tube for radiating X-rays and an X-ray detector for detecting transmitted X-rays, which are arranged to face each other and are supported on each end of a support arm, as well as an X-ray imaging system transport mechanism, which transports the X-ray imaging systems considering a common coordinate system having a mechanical center (isocenter) of the device as a reference point. In particular, such a radiographic X-ray device includes: a shape data registering means of each X-ray imaging system for registering external shape data of three dimensional models corresponding to three dimensional shapes of objects; a positional relation detecting means for detecting out in real time information regarding positional relations of the X-ray imaging systems based on the current position of each X-ray imaging system and external shape data of a three dimensional model; and an imaging system transport control means for controlling the X-ray imaging system transport mechanism in accordance with the information regarding the positional relations of the imaging apparatuses detected by the positional relation detecting means.

Operation and effect: In the device of the above implementation, the external shape data of a three dimensional model that corresponds to the three dimensional shape of each X-ray imaging system is registered into a shape registering means in advance. In an actual radiographic process, the positional relation detecting means detect in real time the information regarding the positional relations of the X-ray imaging systems based on the current position of each X-ray imaging system and the three dimensional external shape data, and the imaging system transport control means controls the X-ray imaging system transport mechanism in accordance with the information regarding the positional relations of the X-ray imaging systems, while the X-ray imaging system is being transported by the X-ray imaging system transport mechanism so as to be set in the imaging orientation and position to meet the needs of imaging studies considering the common coordinate system having the center of the device (isocenter) as the reference point. The X-ray imaging system transport mechanism transports the X-ray imaging systems under the control of the imaging system transport control means.

Therefore, in the above implementation, the information regarding the positional relations between the X-ray imaging system transport mechanisms detected in real time by the positional relation detecting means is based on the three dimensional model external shape data that corresponds to the three dimensional shape of each X-ray imaging system, thoroughly representing the overall current status of the positional relations of external surfaces of both X-ray imaging systems where contacts may occur, and is also based on the current positions of both X-ray imaging systems transported considering the common position coordinate system using the isocenter of the device as the reference point, so that the information regarding the positional relations between the X-ray imaging system transport mechanisms detected by the positional relation detecting means is accurate. Moreover, since the imaging system transport control means controls the X-ray imaging system transport mechanism considering the information of the positional relations of the X-ray imaging systems detected in real time by the positional relation detecting means, the motions of the X-ray imaging systems by the X-ray imaging system transport mechanism thoroughly represent the overall current status of the relation between the external surfaces of the X-ray imaging systems where possible contacts may occur. Further, in addition to the fact that the registration of the external shape data of the three dimensional models to the shape data registration means can be conducted as a conventional data registration process, the detecting of the information regarding the positional relations of the X-ray imaging systems by the positional relation detecting means can be conducted using a conventional arithmetic process algorithm, while both the processes of the registration of the three dimensional external shape data and the detecting of the information regarding the positional relations of the X-ray imaging systems can be done without any specific difficulties.

Therefore, according to the first implementation of the present invention, the positional relation detecting means detects in real time the information regarding the positional relations between the X-ray imaging systems that thoroughly represent the overall current status of the positional relations of external surfaces of both X-ray imaging systems where contacts may occur, the imaging system transport control means is constituted in such a way as to control each X-ray imaging system transport mechanism based on the information regarding the positional relations of the X-ray imaging systems detected by the positional relation detecting means, so that the current status of the positional relations of external surfaces of both X-ray imaging systems can be thoroughly reflected upon the motions of X-ray imaging systems driven by the imaging system transport systems without any difficulty thus preventing any contacts of X-ray imaging systems without fail.

A second implementation of the present invention is a radiographic X-ray device in which said X-ray imaging system transport mechanism is constituted in such a way as to change the current positions of the X-ray imaging systems by rotating or translating the support arm of each X-ray imaging system.

Operation and effect: According to the second implementation, the shooting direction of radiography can be adjusted by rotating the supporting arm on which the X-ray tube and the X-ray detector are mounted and the shooting position of radiography can be adjusted by translating the supporting arm on which the X-ray tube and the X-ray detector are mounted.

A third implementation of the present invention is a radiographic X-ray device in which at least one of said X-ray imaging systems is constituted in such a way as to be capable of changing the arrangement of its X-ray tube and its X-ray detector on the supporting arm for fine tuning the mode of imaging process as well as to accompany a change in the external shape of said X-ray imaging system in accordance with said change in the arrangement of its X-ray tube and its X-ray detector; and, in addition, said positional relation detecting means detects the information regarding the positional relations of the X-ray imaging systems in accordance with said change in the external shape of said X-ray imaging system.

Operation and effect: According to the third implementation, the arrangement of the X-ray tube and/or the X-ray detector on the supporting arm is changeable in order to provide a fine adjustment of the radiography setup, and any changes in the external shape of the X-ray imaging system due to such changes in the arrangement of the X-ray tube and/or the X-ray detector will be considered in the process of detecting the information regarding the positional relations of the X-ray imaging systems so that the X-ray imaging systems are prevented from any contacts between them.

A fourth implementation of the present invention is a radiographic X-ray device, that includes a top board for carrying bodies being inspected capable of moving relative to the common coordinate system of the X-ray imaging systems having the mechanical center (isocenter) of the device as the reference, wherein said shape data registering means is constituted to register shapes of three dimensional models corresponding to the top plate's external shape; and said positional relation detecting means is constituted is such a way as to detect the information regarding positional relations between the X-ray imaging systems and the top plate based on their current positions and the external shape data of the three dimensional model so that the imaging system transport control means can control the X-ray imaging system transport mechanism in accordance with the information regarding the positional relation between the top plate and the X-ray imaging systems as well.

Operation and effect: According to the fourth implementation, the information regarding the positional relations between the X-ray imaging systems and the top plate as well as between the X-ray imaging systems themselves is considered in controlling the X-ray imaging system transport mechanism, so that any contacts between the X-ray imaging systems and the top plate can be avoided.

A fifth implementation of the present invention is a radiographic X-ray device in which said positional relation detecting means is constituted in such a way as to detect the information regarding the positional relations of the X-ray imaging systems using an algorithm that judges whether there is any physical contact between objects.

Operation and effect: According to the fifth implementation, an algorithm for judging whether any contact can occur between objects is usable in detecting the information regarding positional relations between the X-ray imaging systems by the positional relation detecting means, so that it is easier to detect the information regarding positional relations between the X-ray imaging systems.

A sixth implementation of the present invention is a radiographic X-ray device in which said positional relation detecting means is constituted in such a way as to detect the information regarding the positional relations of the X-ray imaging systems using an algorithm that calculates the minimum distance between the objects.

Operation and effect: According to the sixth implementation, an algorithm for calculating the minimum distance between objects is usable in detecting the information regarding positional relations between the X-ray imaging systems by the positional relation detecting means, so that it is easier to detect the information regarding positional relations between the X-ray imaging systems.

DETAILED DESCRIPTION OF THE PREFERRED EMBODIMENTS

Figure 1A:
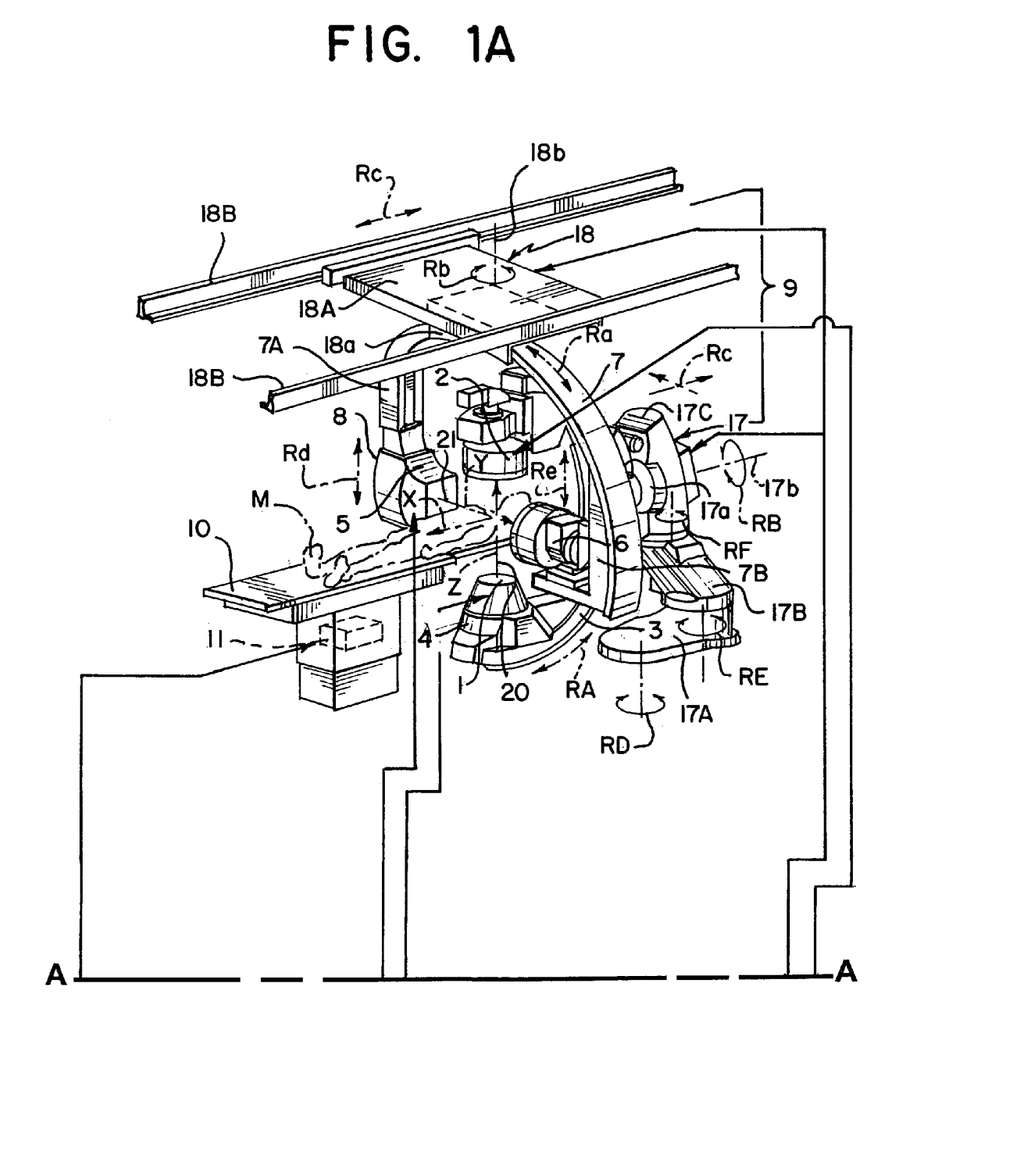
FIGS. 1A and 1B are block diagrams showing the overall constitution of a radiographic X-ray device according to an embodiment of the invention.
Figure 1B:
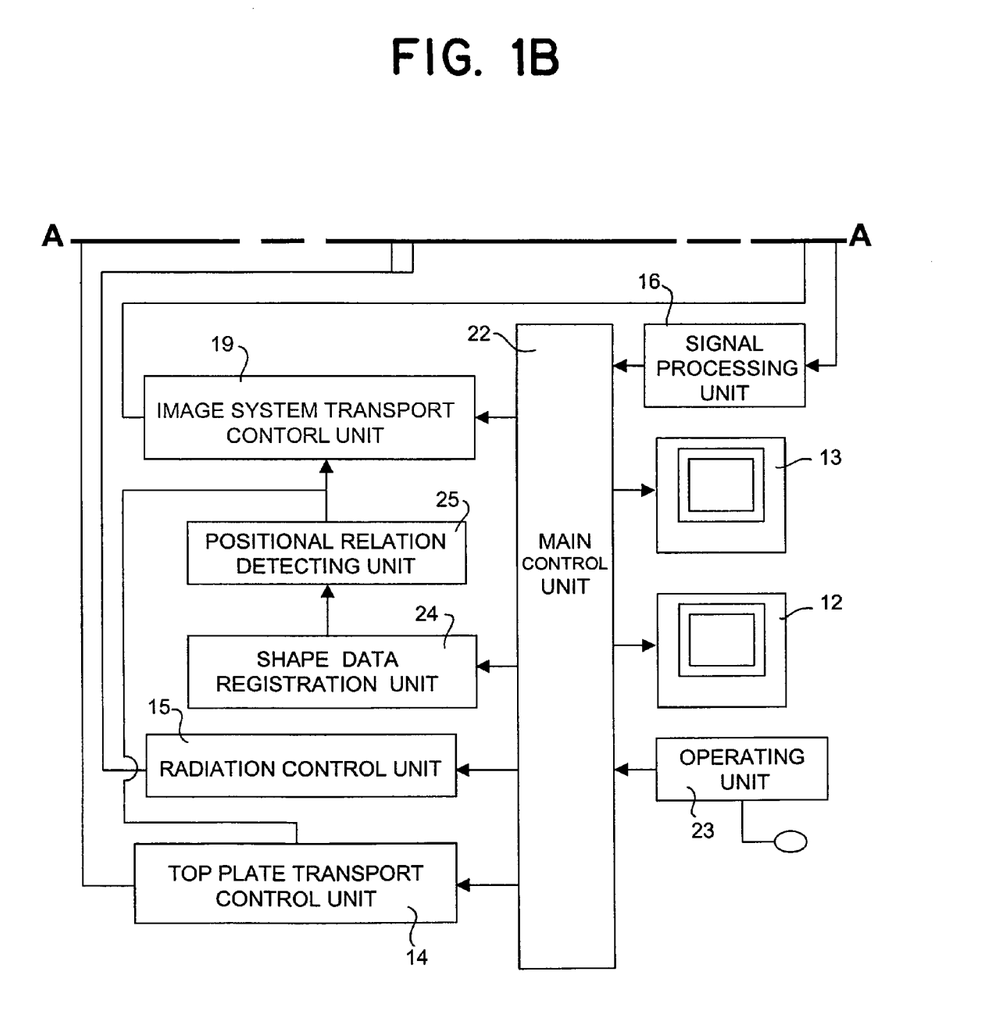

An embodiment of the radiographic X-ray device according to the present invention is described below. FIGS. 1A and 1B are block diagrams showing the overall constitution of the radiographic X-ray device of the embodiment.

The radioscopic imaging device according to the embodiment is, as shown in FIGS. 1A and 1B, a device of the double X-ray imaging system method comprising: a first floor-mounted X-ray imaging system 4 equipped with an X-ray tube 1 for radiating X-rays and an image intensifier (I.I. tube) 2, or an X-ray detector for detecting transmitted X-rays, which are arrange to face each other and are mounted on each end of a C-shaped arm 3; and a second overhead traveling X-ray imaging system 8 equipped with an X-ray tube 5 for radiating X-rays and an image intensifier (I.I. tube) 6, or an X-ray detector for detecting transmitted X-rays, which are arrange to face each other and are mounted on each end of a C-shaped arm 7; as well as an X-ray imaging system transport mechanism 9 for transporting X-ray imaging system 4 and 8 relative to a common coordinate system having the mechanical center (isocenter) of the device as the reference point, wherein X-ray imaging systems 4 and 8 are moved respectively by means of X-ray imaging system transport mechanism 9, thus causing changes to the current positions of X-ray imaging systems 4 and 8 so that the orientations (shooting directions) and positions (shooting positions) of X-ray imaging systems 4 and 8 for radiographic shooting of specimen body M on top plate 10 can be set independently to meet the needs of image studies.

The position coordinate system for determining the current positions of first and second X-ray imaging systems 4 and 8, which has the isocenter Q of the device as the origin (reference point), is an XYZ orthogonal coordinate system where X being the longitudinal (head-toe) direction of a top plate 10, Y being the lateral (left-right) direction of a top plate 10, and Z being the vertical direction as shown in FIGS. 1A and 1B. Top plate 10 is also descried of its current position in relation to the common XYZ orthogonal coordinate system as for X-ray imaging systems 4 and 8, and is transported in each direction of X, Y and Z by means of a top plate transport apparatus 11.

The device of the embodiment also comprises a first image monitor 12 for displaying the radioscopic image of the specimen body M taken by first X-ray imaging system 4 and a second image monitor 13 for displaying the radioscopic image of the specimen body M taken by second X-ray imaging system 8.

The device of the embodiment is constituted in such a way that, after transporting top plate 10 carrying the specimen body M by a top plate transport apparatus 11 so that the specimen body M is placed between X-ray tubes 1 and 5 as well as between I.I. tubes 2 and 6, X-ray imaging system transport mechanism 9 transports first and second X-ray imaging systems 4 and 8 to set their orientations and positions to suit the purpose of radiography; X-ray tubes 1 and 5 irradiate the specimen body M on top plate 10 with X-rays under the control of a radiation control unit 15; and X-ray radioscopy or radiography images are generated from the X-ray detection signals emitted by I.I. tubes 4 and 7 as they are processed by a signal processing unit 16, which are then displayed on first and second image monitors 12 and 13.

The details of the constitution of the X-ray radioscopy device of the embodiment are described below.

X-ray imaging system transport mechanism 9 comprises a first X-ray imaging system transport mechanism 17 that transports first X-ray imaging system 4 and a second X-ray imaging system transport mechanism 18 that transports second X-ray imaging system 8, and X-ray imaging system transport mechanisms 17 and 18 transport X-ray imaging systems 4 and 8 under the control of an imaging system transport control unit 19.

First X-ray imaging system transport mechanism 17 moves first X-ray imaging system 4 in various ways by rotating or translating C-shaped arm 3. With the motion of first X-ray imaging system 4, the current position of first X-ray imaging system 4 changes. As for the possible modes of rotations of C-shaped arm 3 to be caused by first X-ray imaging system transport mechanism 17, one is a "slide rotation" in which C-shaped arm 3 rotates in the direction shown by an arrow RA along the bend of the arm circumventing the isocenter Q along the arm's longitudinal direction, and the other is a "sagittal rotation" in which C-shaped arm 3 rotates in the direction of arrow RB in such a way that a supporting shaft 17a that supports C-shaped arm 3 in the middle of its back rotates around an axis 17b while axis 17b always passes through the isocenter Q. In both the slide rotation and the sagittal rotation, an X-ray axis 20 that connects the center of X-ray tube 1 with the center of I.I. tube 2 with the rotation of C-shaped arm 3 changes its angle as C-shaped arm 3 rotates, thus causing a change in the direction of radiographic shooting, while the direction of the angular change of X-ray axis 20 differs by 90 degrees between the slide rotation and the sagittal rotation, so that it is possible to create a variety of adjustments in the shooting angle.

Moreover, a mode of translation of C-shaped arm 3 according to first X-ray imaging system transport mechanism 17 is a horizontal translation in which the entire arm moves parallel to the direction shown by an arrow RC (X direction or Y direction). In the case of first X-ray imaging system transport mechanism 17, three holding blocks 17A–17C are linked together, or piled up, so that the horizontal translation shown by the arrow RC is accomplished by combining the individual rotations of three holding blocks 17A through 17C in the directions of RD through RF respectively in an appropriate manner. As C-shaped arm 3 makes a horizontal translation, the position of X-ray axis 20 also makes a horizontal translation in the same direction thus allowing it to assume a variety of shooting positions.

Moreover, the system is so constituted that the amount of rotation in the directions of the arrows RA and RB and the amount of rotation in the directions of the arrows RD through RF (corresponding to the amount of translation in the direction of the arrow RC) of first X-ray imaging system transport mechanism 17 are detected by appropriate sensors (not shown), and the results of the detections are fed back to imaging system transport control unit 19 as well as to other places of the control system where such information is needed as the information concerning the current position of first X-ray imaging system 4.

Second X-ray imaging system transport mechanism 18 moves second X-ray imaging system 8 in various ways by rotating or translating C-shaped arm 7. With the motion of second X-ray imaging system 8, the current position of second X-ray imaging system 8 changes. As for the possible modes of rotations of C-shaped arm 7 to be caused by second X-ray imaging system transport mechanism 18, one is a "slide rotation" in which C-shaped arm 7 rotates in the direction shown by an arrow Ra along the bend of the arm circumventing the isocenter Q along the arm's longitudinal direction, and the other is a "sagittal rotation" in which C-shaped arm 7 rotates in the direction of arrow Rb in such a way that a supporting shaft 18*a* that supports C-shaped arm 7 in the middle of its back rotates around an axis 18*b* while axis 18*b* always passes through the isocenter Q. In both the slide rotation and the sagittal rotation, an X-ray axis 21 that connects the center of X-ray tube 5 with the center of I.I. tube 6 with the rotation of C-shaped arm 7 changes its angle as C-shaped arm 7 rotates, thus causing a change in the direction of radiographic shooting, while the direction of the angular change of X-ray axis 21 differs by 90 degrees between the slide rotation and the sagittal rotation, so that it is possible to create a variety of adjustments in the shooting angle.

One of the possible motions of C-shaped arm 7 according to second X-ray imaging system transport mechanism 18 is a translation in the direction of an arrow Rc, i.e., a motion parallel to the X-axis direction. More specifically, a carriage 18A that hangs C-shaped arm 7 from the ceiling via a support shaft 18*a* travels along rails 18B and 18B, which extend in the X-axis direction on the ceiling, so that C-shaped arm 7 travels horizontally in the X-axis direction as carriage 18A travels along rails 18B and 18B. As C-shaped arm 7 makes a horizontal translation, the position of X-ray axis 21 also makes a horizontal translation in the same direction thus allowing it to assume a variety of shooting positions.

Moreover, the system is so constituted that the amount of rotation in the directions of the arrows Ra and Rb as well as the amount of translation in the direction of the arrow Rc of second X-ray imaging system transport mechanism 18 is detected by appropriate sensors (not shown) and the result of the detection is fed back to imaging system transport control unit 19 as well as to other places of the control system where such information is needed as the information representing the current position of second X-ray imaging system 8.

In the case of second X-ray imaging system 8, C-shaped arm 7 is so constituted as to allow fine adjustments of the shooting position (shooting mode) in the Z-axis direction by means of varying the arrangements of X-ray tube 5 and I.I. tube 6 on C-shaped arm 7 by means of allowing only hands 7A and 7B provided on both ends of C-shaped arm 7 to extend or contract for equal distances in the directions of arrows Rd and Re, i.e., parallel to the Z-axis. It is also constituted in such a way that the arrangements of X-ray tube 5 and I.I. tube 6 are changed in accordance with the XYZ coordinate system, the amounts of translations of hands 7A and 7B are detected by appropriate sensors (not shown), and the results of the detections are fed back to imaging system transport control unit 19 as well as to other places of the control system where such information is needed as the changes in the arrangement of X-ray tube 5 and I.I. tube.

Moreover, in the case of first and second X-ray imaging systems 4 and 8, X-ray tubes 1 and 5 are fixed on C-shaped arms 3 and 7, while I.I. tubes 2 and 6 are mounted on C-shaped arms 3 and 7 to be able to move for a short distance along the X-ray axes 20 and 21, so that the shooting magnification of radiography can be adjusted by changing the magnification of transmitted X-ray images projected on the X-ray detection surfaces of I.I. tubes 2 and 6 by moving I.I. tubes 2 and 6 in the directions of X-ray axes 20 and 21. It is so constituted that the amount of movements of I.I. tubes 2 and 6 are detected by appropriate sensors (not shown), and the results of the detections are fed back to imaging system transport control unit 19 as well as to other places of the control system where such information is needed as the information representing the current positions of I.I. tubes 2 and 6.

Depending on the input operation via an operating unit 23 and the progress of radiography operations, a main control unit 22 of the device of the embodiment is constituted to issue instructions and data required by radiation control unit 15 for controlling X-ray radiation by X-ray tubes 1 and 5, imaging system transport control unit 19 for controlling first and second X-ray imaging system transport mechanisms 17 and 18, or top plate transport control unit 14 for controlling top plate transport apparatus 11.

In order to securely avoid contacts between first and second X-ray imaging systems 4 and 8, the radiographic X-ray device of the embodiment is constituted in such a ways as to comprise a shape data registration unit 24 for registering the data of three dimensional model external shapes that correspond to the three dimensional shapes of X-ray imaging systems 4 and 8, and a positional relation detecting unit 25 for detecting in real time the positional relations between X-ray imaging systems 4 and 8 based on the current positions and the three dimensional model external shape data of X-ray imaging systems 4 and 8, wherein imaging system transport control unit 19 controls first and second X-ray imaging system transport mechanisms 17 and 18 considering the information regarding positional relations between X-ray imaging systems 4 and 8 detected by positional relation detecting unit 25, the features of which will be described below in detail.

Shape data registration unit 24 has the pre-registered data for the three dimensional external shapes that correspond to the three dimensional external shapes of X-ray imaging systems 4 and 8 according to the following process.

The first step is to prepare external shape data in the STL (Standard Triangle Language) format for the three dimensional models that present shapes that are essentially similar to the external three dimensional shapes of first and second X-ray imaging system transport mechanisms 17 and 18. Since the STL format is to describe a desired three dimensional shape in terms of a group of triangles, the external shape data of a three dimensional model is stored as a group of coordinates of all three apexes of each triangle on an orthogonal coordinate system, so that it is possible to represent the three dimensional model shapes that correspond to the three dimensional shapes of C-ray imaging apparatuses 4 and 8 with a relatively small amount of data.

The external shape data of three dimensional models in the STL format can be easily produced, for example, by applying the STL data conversion technique to the three dimensional CAD data that accurately represent the shapes that are similar to the external shapes of first and second X-ray imaging system transport mechanisms 17 and 18 that are produced during the process of designing first and second X-ray imaging system transport mechanisms 17 and 18.

Figure 2:
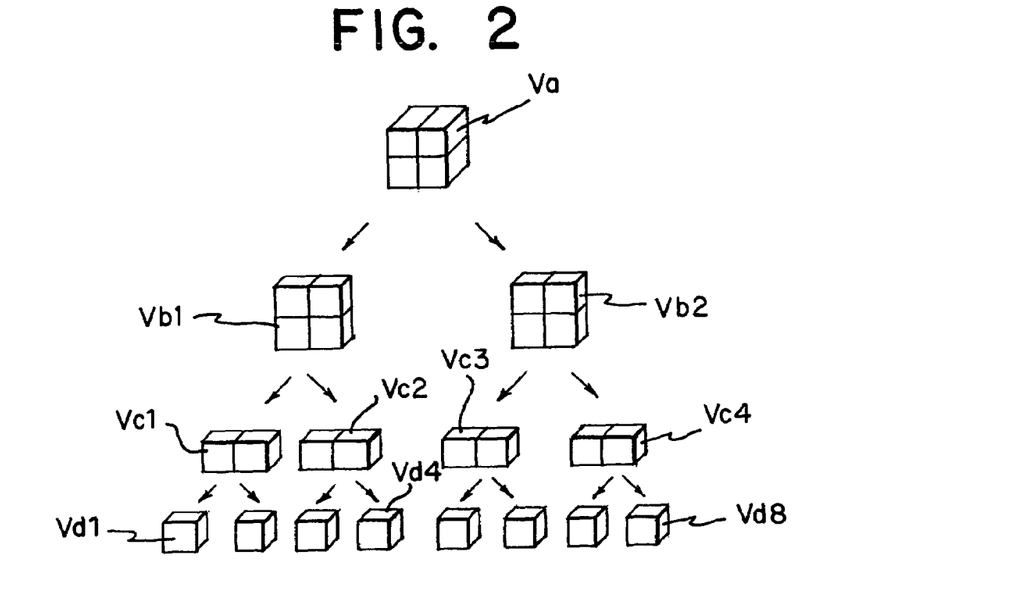
FIG. 2 is a concept drawing for describing a VOXEL type format of external data of a three dimensional model.

Next, the external shape data of the three dimensional models in the STL format is converted into data in VOXEL (Volume Pixel) format. The data conversion in the VOXEL format, as shown in FIG. 2, is essentially to set up a parent box Va, either a cube or a rectangular solid, that completely contains the external shape data of a three dimensional model expressed in the STL format within a three dimensional virtual space, break it up into children boxes Vb1 and Vb2, either cubes or rectangular solids, grandchildren boxes Vc1 through Vc4, great-grandchildren Vd1 through Vd8, and so on down in multiple stages until the process reaches the final step to obtain the smallest boxes, and obtain the data containing information that shows whether each of the smallest boxes has any external shape data of the three dimensional model. The size of the smallest box is typically a one centimeter cube in the case of the actual dimensions of first and second X-ray imaging system transport mechanisms 17 and 18.

Whether the smallest box contains any external shape data of a three dimensional model is determined by checking all the boxes on each step to see whether each of them has any external shape data of the three dimensional model repeatedly. The process can be accelerated by deciding not to check boxes of any further levels after a box on a certain level is determined to contain no external data of the three dimensional model (No), as it is obvious that boxes generated by dividing said box any further cannot possibly contain any data.

Figure 3:
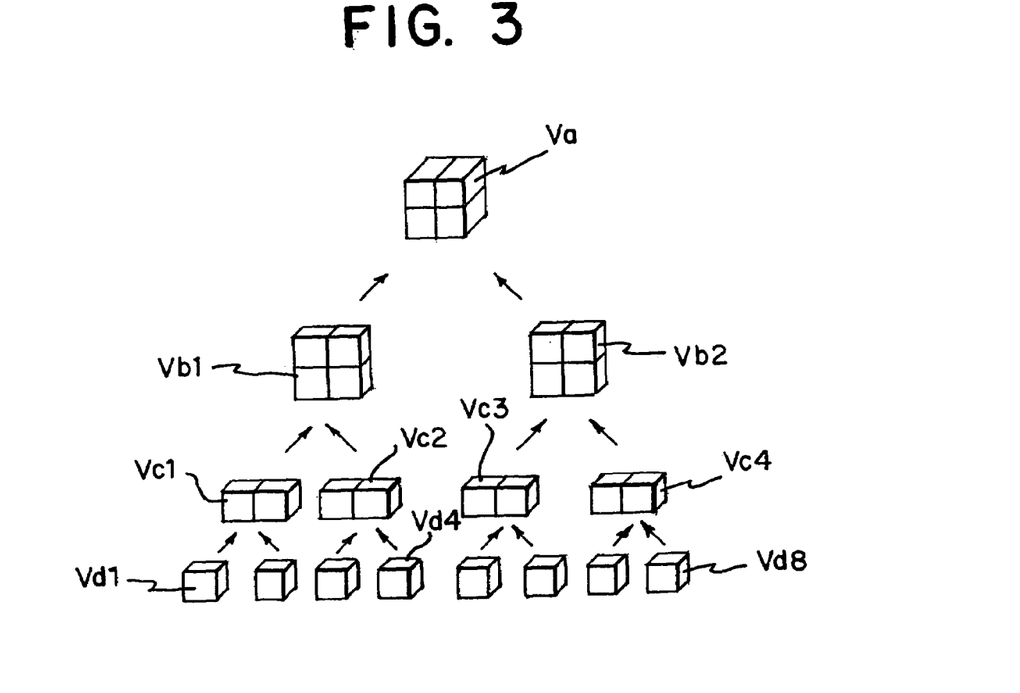
FIG. 3 is a concept drawing for describing a BSP tree type format of external data of a three dimensional model.

Next, the VOXEL format data is converted into BSP (binary separated partition) tree data. The data conversion to the BSP tree data shown in FIG. 3, contrary to a case of FIG. 2, corresponds to the case of combining the smallest boxes back to the original parent box containing the data containing information at the final division stage. In other words, in the case of the BSP tree data, the three dimensional external shape of first and second X-ray imaging systems 4 and 8 is expressed in a group of boxes attached with data containing information. The external shape data of the three dimensional model in the BSP tree format is registered into shape data registration unit 24 in advance.

The external data of the three dimensional model does not have to represent the entirety of the three dimensional external shapes of X-ray imaging systems 4 and 8, eliminating the data of areas where there is no chance of contacts with each other. In the case of the device of the embodiment, the burden of the arithmetic process for detecting the relative position information can be reduced by eliminating the areas where there is no chance of contacts with each other.

Positional relation detecting unit 25 detects the information regarding the relative position relations between X-ray imaging systems 4 and 8 based on the current positions and the external shape data of the three dimensional models, which are registered in shape data registration unit 24, of first and second X-ray imaging systems 4 and 8 using an algorithm for judging whether the objects are in positional relations to cause contacts. More specifically, the two boxes of the external shape data of the three dimensional models in the BSP tree format corresponding to the external shapes of X-ray imaging systems 4 and 8 are rotated and translated in a virtual three dimensional space based on the current positions of first and second imaging apparatuses 4 and 8 in accordance with the motions of first and second imaging apparatuses 4 and 8. This causes the two boxes for the external data of the three dimensional models to occupy always the same positions as first and second X-ray imaging systems 4 and 8 in the virtual three dimensional space, and thoroughly represent the current status of relations between the external surfaces of X-ray imaging systems 4 and 8, where collisions between X-ray imaging systems 4 and 8 may occur.

Next, the presence or lack of contacts between the smallest boxes of the external shape data of the three dimensional model. Of course, since X-ray imaging systems 4 and 8 do not collide with each other under a normal situation, the expected judgment is always "no contact exists"; however, if it results in a judgment that "a contact exists," it means that the contact has already occurred and that the system failed to avoid it. Therefore, a certain virtual contact distance is preset, which allows the system a margin for contact prevention, in checking the presence of collisions, and the distance between a smallest box of one of the external shape data of the three dimensional models and a smallest box of the other external data of the three dimensional models, so that it is judged that there is a contact if the distance is smaller than the virtual contact distance, and that there is no contact if the distance is larger than the virtual contact distance. The distance calculation and the judgment process mentioned above are repeated for all smallest boxes accompanied with data containing information (containing data). There is no need for conducting distance calculation and judgment on smallest boxes not accompanied with data containing information (not containing data) as they do not involved in any contact.

The result of these judgments on the presence of contacts between X-ray imaging systems 4 and 8 is issued immediately to imaging system transport control unit 19. The judgment result on where there is any contact as the information regarding positional relation is extremely accurate as it is based on the current positions of first and second X-ray imaging systems 4 and 8 that are moved in accordance with the common coordinate system having the isocenter Q as the reference point.

In the case of the device of the embodiment, imaging system transport control unit 19 is constituted in such a way that no action is taken if the content of the received information infers no contact, while a control signal is issued to instruct an immediate halt if X-ray imaging systems 4 and 8 are in motion and the content of the received information infers contact(s).

In the device of this invention, it can be constituted to allow the X-ray imaging systems to remain in motions by ordering one of the X-ray imaging systems to retract, instead of stopping the moving X-ray imaging systems, when the received information infers the existence of contact(s).

Moreover, positional relation detecting unit 25 is constituted in such a way as to detect the information regarding the positional relations between X-ray imaging systems 4 and 8 considering the external shape changes of X-ray imaging system 8 when the changes occur in the arrangement of X-ray tube 5 and I.I. tube 6 due to a fine adjustment of shooting magnification by means of extracting or contracting only the hands 7A and 7B provided at both ends of C-shaped arm 7. When external shape changes occur in X-ray imaging system 8 due to the changes in the arrangement of X-ray tuber 5 and I.I. tube 6 on C-shaped arm 7, the positional relations of the external surfaces of the X-ray imaging systems change so that it may result in an error if the information regarding the positional relation is sought for. Therefore, the information regarding the positional relations between X-ray imaging systems 4 and 8 is sought for considering the external shape change of X-ray imaging system 8 due to the change in the arrangement of X-ray tuber 5 and I.I. tuber 6.

In the case of the device of the embodiment, the external shape data of the three dimensional model in the BSP tree format for X-ray imaging system 8 is registered by registering X-ray tube 5, I.I. tuber 6 and C-shaped arm 7 separately so that the contact judgment can be conducted after moving the boxes that constitute the external data of the three dimensional models of X-ray tube 5 and I.I. tuber 6 separately depending on the change in the arrangement of X-ray tube 5 and I.I. tuber 6.

The device of the embodiment is further constituted in such a way that it can securely avoid the contact of first and second X-ray imaging systems 4 and 8 with top plate 10. In other words, it is constituted in such a way that the external shape data of the three dimensional model that corresponds to the three dimensional external shape of top plate 10 is registered to shape data registration unit 24 in a similar manner as in the case of the X-ray imaging systems, and that positional relation detecting unit 25 detects the presence or lack of contacts between top plate 10 and X-ray imaging systems 4 and 8 as information regarding the positional relations based on the current positions and the external shape data of three dimensional models of al the members in a similar process as the case of the X-ray imaging systems, so that imaging system transport control unit 19 controls first and second X-ray imaging system transport mechanisms 17 and 18 considering the information regarding the positional relations between top plate 10 and X-ray imaging systems 4 and 8.

Moreover, in the device according to the embodiment, the information regarding the positional relations between top plate 10 and X-ray imaging systems 4 and 8 is issued to top plate transport control unit 14 as well, so that top plate transport control unit 14 controls top plate transport apparatus 11 considering the information regarding the positional relations between top plate 10 and X-ray imaging systems 4 and 8. Since it is a common practice not to move top plate 10 once it is set in a standard position, it can be constituted in such a way that the information regarding the positional relations between top plate 10 and X-ray imaging systems 4 and 8 is not issued to top plate transport control unit 14.

Imaging system transport control unit 19 and top plate transport control unit 14 are so constituted that whenever the received information infers that there is a contact between top plate 10 and X-ray imaging systems 4 and 8, they issue signals to halt the transport between top plate 10 and X-ray imaging systems 4 and 8.

In the device of this invention, it can also be constituted to allow the X-ray imaging systems or the top plate to remain in motions by ordering one of the X-ray imaging systems or the top plate that may cause interference with one of the X-ray imaging systems or the top plate to retract.

Figure 4:
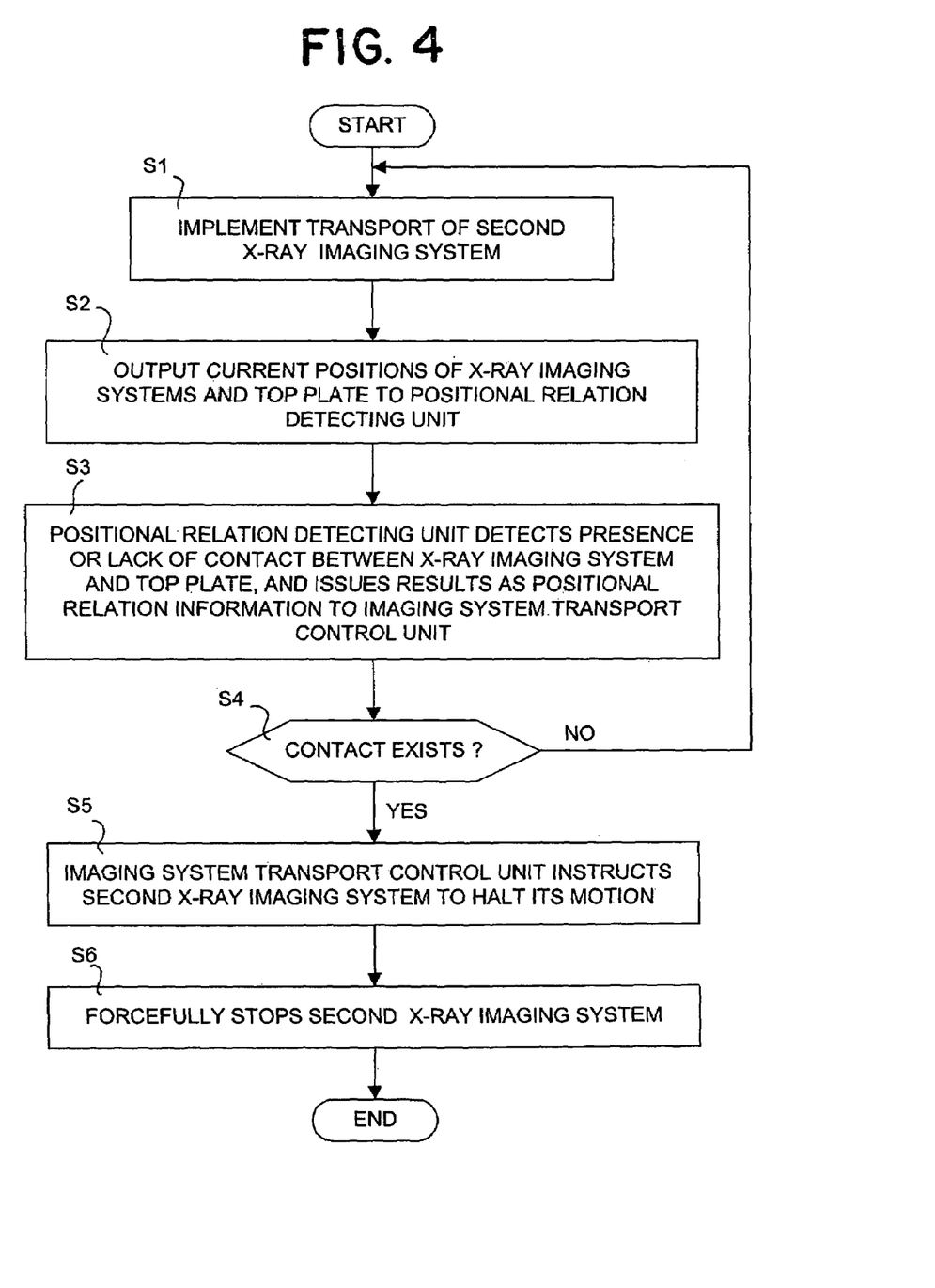
FIG. 4 is a flowchart showing a contract avoiding process in the case of moving an X-ray imaging system in the embodiment device.
Figure 5A:
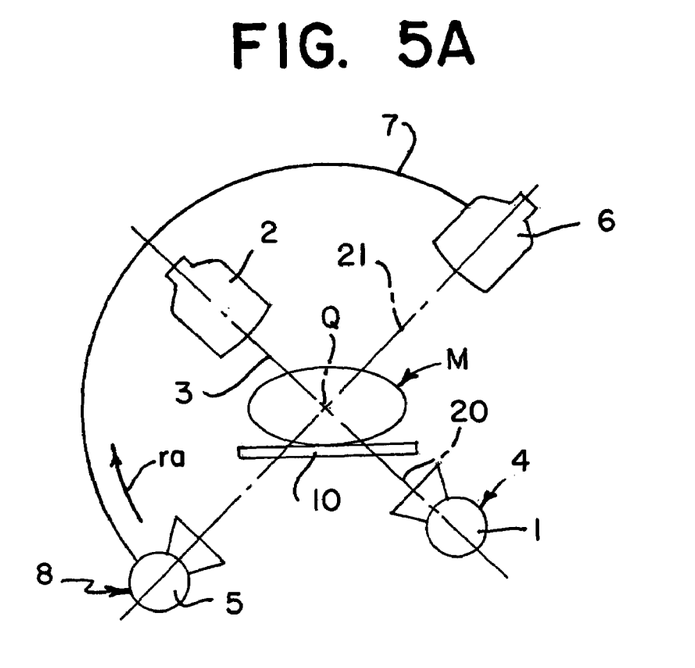
FIGS. 5A, 5B and 5C are schematic diagrams showing an example of motions of X-ray imaging systems in the embodiment device.

Next, let us explain referring to the accompanying drawings how the possible contact is avoided while X-ray imaging systems 4 and 8 are in motion in the case of the above embodiment. FIG. 4 is a flowchart showing the process of avoiding contacts for first and second X-ray imaging systems 4 and 8 in the device according to the embodiment. As shown in FIG. 5A, in the case when X-ray axes 20 and 21 of X-ray imaging systems 4 and 8 are on the same plane that pass through the isocenter Q, C-shaped arm 7 of second X-ray imaging system 8 is slidingly rotated to move X-ray imaging system 8 while maintaining first X-ray imaging system 4 stationary.

Step S1: Second X-ray imaging system 8 starts to move in the direction of arrow "ra" with the start of the sliding rotation of C-shaped arm 7.

Step S2: First and second imaging transport apparatuses 17 and 18 detect the current positions of X-ray imaging systems 4 and 8 and report them to positional relation detecting unit 25, while top plate transport apparatus 11 detects the current position of top plate 10 and reports it to positional relation detecting unit 25.

Step S3: Positional relation detecting unit 25 investigates if there is any contact between X-ray imaging systems 4 and 8 as well as between top plate 10 and X-ray imaging systems 4 and 8 based on the current positions of top plate 10 and X-ray imaging systems 4 and 8 as well as the external shape data of their respective three dimensional models, and the result of said investigation is reported to imaging system transport control unit 19 as the information regarding the positional relations.

Figure 5B:
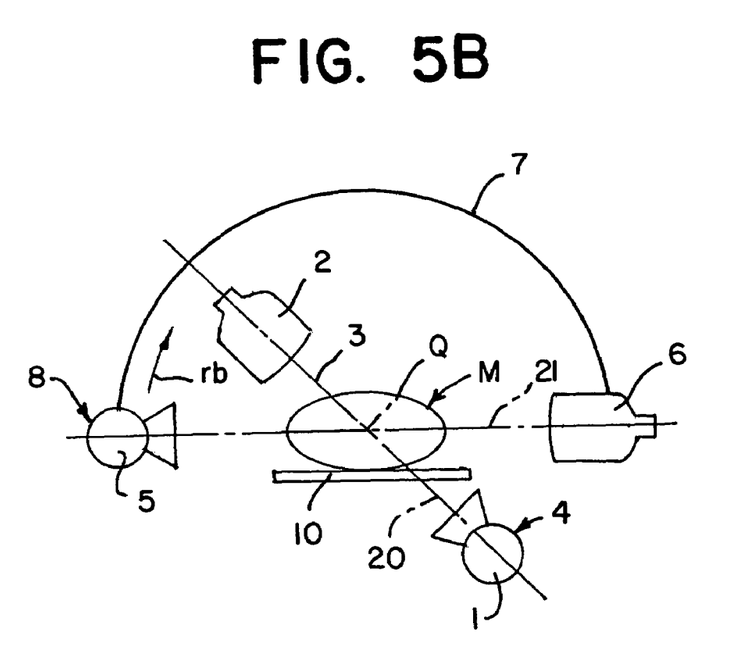

Step S4: If the information infers no contact, it returns to step S1 and allows C-shaped arm 7 to continue its sliding rotation as shown in FIG. 5B, and allows second X-ray imaging system 8 to move in the direction shown by arrow "rb." If the received information infers a contact, it proceeds' to the next step, S5.

Step S5: Imaging system transport control unit 19 sends a control signal to instruct second X-ray imaging system transport mechanism 18 to halt the motion of second X-ray imaging system 8.

Figure 5C:
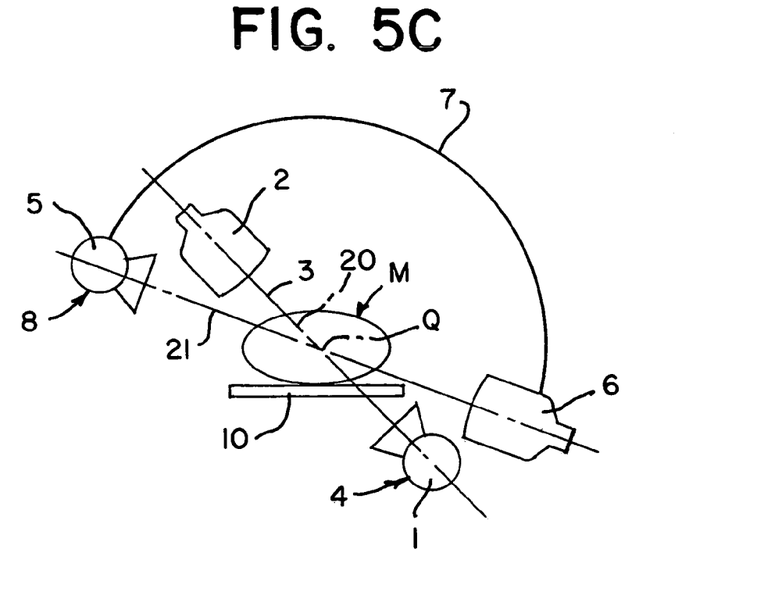

Step S6: Upon receiving the control signal for motion halt, second X-ray imaging system transport mechanism 18 immediately reduces the speed of and stops the motor (not shown) that drives C-shaped arm 7, second X-ray imaging system 8 is forced to stop just before first X-ray imaging system 4 and second X-ray imaging system 8 come into contact with each other as shown in FIG. 5C. Thus, the situation of first X-ray imaging system 4 and second X-ray imaging system 8 come into contact with each other is avoided.

As can be seen from the detailed description in the above, the X-ray radioscopic device of the embodiment is constituted in such a way that positional relation detecting unit 25 detects in real time the information regarding the positional relations between first and second X-ray imaging systems 4 and 8 as well as between top plate 10 and X-ray imaging systems 4 and 8, which thoroughly describes the current situation of the arrangement of the external surfaces of top plate 10 and X-ray imaging systems 4 and 8 where collisions may occur between top plate 10 and X-ray imaging systems 4 and 8, and that top plate transport control unit 14 and imaging system transport control unit 19 control the movements of top plate 10 and X-ray imaging systems 4 and 8 considering the information regarding the positional relations between top plate 10 and X-ray imaging systems 4 and 8 detected by positional relation detecting unit 25, thus allowing the arrangement and the current status of the external surfaces of top plate 10 and X-ray imaging systems 4 and 8 to be precisely reflected upon the movements of top plate 10 and X-ray imaging systems 4 and 8 thoroughly, precisely and with no difficulty, so that any contact between top plate 10 and X-ray imaging systems 4 and 8 can be avoided securely.

In the case where the system is constituted, as in the device of the present embodiment, in such a way that the preparation of the external shape data of the three dimensional model to be registered in shape data registration unit 24 is based on the CAD data used in the designing stage, there is an advantage that the updating of the external shape data of the three dimensional model, which is required for a newly designed X-ray imaging system, can be easily accomplished by simply re-registering the external shape data of the three dimensional model based on the CAD data used in the new design.

The present invention is not limited to the above embodiment, but rather can be modified for implementation.

(1) Although an algorithm for determining if objects are in a positional relation which is likely to cause a contact is used in detecting pertinent information regarding positional relations of the objects in the above embodiment device, a device that uses an algorithm for calculating the minimum distance between objects in detecting pertinent information regarding positional relations of the object can be proposed as an alternative approach. In the case of a device of the abovementioned alternative method, the burden of arithmetic operation for distance calculation can be reduced by limiting the calculation to the vicinity of a point where the minimum distance occurred in the latest calculation as the point where the minimum distance is occurring now between the objects should be close to the point where the minimum distance occurred in the latest calculation.

(2) In the case of the embodiment device, the three dimensional external shapes of first and second X-ray imaging systems 4 and 8 change, but only slightly, when I.I. tubes 2 and 6 move slightly along the X-ray axes 20 and 21 for adjusting the image magnification, so that it is not considered in detecting the information regarding the positional relations as the shape change is so small. However, the system can also be constituted in such a way as to take into consideration such a change in the external three dimensional shapes of first and second X-ray imaging systems 4 and 8 due to the motions of I.I. tubes 2 and 6 in adjusting the image magnification.

(3) Although the embodiment device is constituted in such a way as to detect the information of the positional relations between top plate 10 and X-ray imaging systems 4 and 8, there are cases where there is no chance of contacts between top plate 10 and X-ray imaging systems 4 and 8, practically speaking, depending on how top plate 10 and X-ray imaging systems 4 and 8 moves, so that a device that does not detect the information of the positional relations between top plate 10 and X-ray imaging systems 4 and 8 can be quoted here as an alternative.

(4) Although the embodiment device is constituted to have a floor mounted type and an overhead traveling type of X-ray imaging systems, the device can have all floor mounted type, all overhead traveling type, or one or more floor traveling type of X-ray imaging systems.

(5) Although the embodiment device uses I.I. tubes as the X-ray detectors, flat panel type X-ray detectors (FPD) can be used as X-ray detectors.

(6) Although the embodiment device uses two sets of X-ray imaging systems, the device may not be limited to two sets. For example, it may have three or four sets of X-ray imaging systems.

(7) Although the embodiment device is a medical device, the device according this invention can be used for industrial purposes.

EFFECTS OF THE INVENTION

As can be seen from the above, in the radiographic X-ray device according to the present invention, the positional relation detecting means detects in real time the information regarding the positional relations between the X-ray imaging systems that thoroughly represents the overall current status of the positional relations of external surfaces of both X-ray imaging systems where collisions may occur, the imaging system transport control means is constituted in such a way as to control each X-ray imaging system transport mechanism based on the information regarding the positional relations of the X-ray imaging systems detected by the positional relation detecting means, so that the current status of the positional relations of external surfaces of both X-ray imaging systems can be thoroughly reflected upon the motions of X-ray imaging systems driven by the imaging system transport mechanisms without any difficulty thus preventing any collisions of X-ray imaging systems without fail.

Although the invention has been described above with reference to the embodiments, the embodiments are not intended to limit the scope of the invention. Many modifications and variations are possible within the scope of the invention and those modifications and variations that may be apparent to a person skilled in the art are intended to be included within the scope of the appended claims.

What is claimed is:

1. A radiographic X-ray device comprising:
   a plurality of X-ray imaging systems each comprising an X-ray tube for radiating X-rays and an X-ray detector for detecting transmitted X-rays, which are arranged to face each other and are mounted on each end of a support arm;
   an X-ray imaging system transport mechanism for transporting the X-ray imaging systems using a common coordinate system having a mechanical center of the device as a reference point;
   a shape data registering means for each X-ray imaging system for pre-registering three dimensional external shape data models corresponding to three dimensional external shape data models of the X-ray imaging system, wherein the models are in a voxel data tree format;
   a positional relation detecting means for obtaining in real time information regarding positional relations of the X-ray imaging systems based on a current position of each X-ray imaging system and the external shape data of the three dimensional model; and
   an imaging system transport control means for controlling the X-ray imaging system transport mechanism in accordance with the information regarding the positional relations of the X-ray imaging systems detected by the positional relation detecting means.

2. A radiographic X-ray device of claim 1, wherein said X-ray imaging system transport mechanism is configured to change the current positions of the X-ray imaging systems by rotating or translating the support arm of each X-ray imaging system.

3. A radiographic X-ray device of claim 2, wherein at least one of said X-ray imaging systems can change the arrangement of its X-ray tube and its X-ray detector on the supporting arm for fine tuning a mode of imaging process and to accompany a change in the external shape of said X-ray imaging system in accordance with said change in the arrangement of its X-ray tube and its X-ray detector; and said positional relation detecting means obtains the information regarding the positional relations of the X-ray imaging systems in accordance with said change in the external shape of said X-ray imaging system.

4. A radiographic X-ray device of claim 2, further comprising:
a top plate for carrying a subject being inspected, said top plate configured to move in reference to the common coordinate system of the X-ray imaging systems having the mechanical center of the device as the reference point,
wherein said shape data registering means further registers shapes of three dimensional models corresponding to the top plate's external shape; and said positional relation detecting means obtains the information regarding positional relations between the X-ray imaging systems and the top plate based on their current positions and the external shape data of the three dimensional model so that the imaging system transport control means can control the X-ray imaging system transport mechanism in accordance with the information regarding the positional relation between the top plate and the X-ray imaging systems.

5. A radiographic X-ray device of claim 2, wherein said positional relation detecting means obtains the information regarding the positional relations of the X-ray imaging systems using an algorithm that judges whether there is any physical contact between the X-ray imaging systems.

6. A radiographic X-ray device of claim 2, wherein said positional relation detecting means obtains the information regarding the positional relations of the X-ray imaging systems using an algorithm that calculates the minimum distance between the X-ray imaging systems.

7. A radiographic X-ray device of claim 1, wherein at least one of said X-ray imaging systems can change the arrangement of its X-ray tube and its X-ray detector on the supporting arm for fine tuning a mode of imaging process and to accompany a change in the external shape of said X-ray imaging system in accordance with said change in the arrangement of its X-ray tube and its X-ray detector; and said positional relation detecting means obtains the information regarding the positional relations of the X-ray imaging systems in accordance with said change in the external shape of said X-ray imaging system.

8. A radiographic X-ray device of claim 7, further comprising:
a top plate for carrying a subject being inspected, said top plate configured to move in reference to the common coordinate system of the X-ray imaging systems having the mechanical center of the device as the reference point,
wherein said shape data registering means further registers shapes of three dimensional models corresponding to the top plate's external shape; and said positional relation detecting means obtains the information regarding positional relations between the X-ray imaging systems and the top plate based on their current positions and the external shape data of the three dimensional model so that the imaging system transport control means can control the X-ray imaging system transport mechanism in accordance with the information regarding the positional relation between the top plate and the X-ray imaging systems.

9. A radiographic X-ray device of claim 7, wherein said positional relation detecting means obtains the information regarding the positional relations of the X-ray imaging systems using an algorithm that judges whether there is any physical contact between the X-ray imaging systems.

10. A radiographic X-ray device of claim 7, wherein said positional relation detecting means obtains the information regarding the positional relations of the X-ray imaging systems using an algorithm that calculates the minimum distance between the X-ray imaging systems.

11. A radiographic X-ray device of claim 1, further comprising:
a top plate for carrying a subject being inspected, said top plate configured to move in reference to the common coordinate system of the X-ray imaging systems having the mechanical center of the device as the reference point,
wherein said shape data registering means further registers shapes of three dimensional models corresponding to the top plate's external shape; and said positional relation detecting means obtains the information regarding positional relations between the X-ray imaging systems and the top plate based on their current positions and the external shape data of the three dimensional model so that the imaging system transport control means can control the X-ray imaging system transport mechanism in accordance with the information regarding the positional relation between the top plate and the X-ray imaging systems.

12. A radiographic X-ray device of claim 11, wherein said positional relation detecting means obtains the information regarding the positional relations of the X-ray imaging systems using an algorithm that judges whether there is any physical contact between the X-ray imaging systems.

13. A radiographic X-ray device of claim 11, wherein said positional relation detecting means obtains the information regarding the positional relations of the X-ray imaging systems using an algorithm that calculates the minimum distance between the X-ray imaging systems.

14. A radiographic X-ray device of claim 1, wherein said positional relation detecting means obtains the information regarding the positional relations of the X-ray imaging systems using an algorithm that judges whether there is any physical contact between the X-ray imaging systems.

15. A radiographic X-ray device of claim 1, wherein said positional relation detecting means obtains the information regarding the positional relations of the X-ray imaging systems using an algorithm that calculates the minimum distance between the X-ray imaging systems.

16. A radiographic X-ray device of claim 1, wherein said positional relation detecting means obtains the information regarding the positional relations of the X-ray imaging systems using an algorithm that calculates the minimum distance between the X-ray imaging systems.

17. A radiographic X-ray device comprising:
an X-ray imaging system comprising an X-ray tube for radiating X-rays and an X-ray detector for detecting transmitted X-rays, which are arranged to face each other and are mounted on each end of a support arm;

an X-ray imaging system transport mechanism for transporting the X-ray imaging system using a coordinate system having a mechanical center of the device as a reference point;

a shape data registering means of the X-ray imaging system for pre-registering three dimensional external shape data models corresponding to three dimensional external shape data models of the X-ray imaging system, wherein the models are in a voxel data tree format;

a positional relation detecting means for obtaining in real time information regarding positional relations of the X-ray imaging system based on a current position of the X-ray imaging system and the external shape data of the three dimensional model; and an imaging system transport control means for controlling the X-ray imaging system transport mechanism in accordance with the information regarding the positional relations of the X-ray imaging system detected by the positional relation detecting means.

18. A radiographic X-ray device of claim 17, further comprising:

a top plate for carrying a subject being inspected, said top plate configured to move in reference to a common coordinate system of the X-ray imaging system having the mechanical center of the device as the reference point, wherein said shape data registering means further registers shapes of three dimensional models corresponding to the top plate's external shape; and said positional relation detecting means obtains the information regarding positional relations between the X-ray imaging systems and the top plate based on their current positions and the external shape data of the three dimensional model so that the imaging system transport control means can control the X-ray imaging system transport mechanism in accordance with the information regarding the positional relation between the top plate and the X-ray imaging system.

19. A radiographic X-ray device comprising:

an X-ray imaging system comprising an X-ray tube for radiating X-rays and an X-ray detector for detecting transmitted X-rays, which are arranged to face each other and are mounted on each end of a support arm;

an X-ray imaging system transport mechanism for transporting the X-ray imaging system using a coordinate system having a mechanical center of the device as a reference point;

a shape data registering means of the X-ray imaging system for pre-registering three dimensional external shape data models corresponding to three dimensional external shape data models of the X-ray imaging system, wherein the models are in a voxel data tree format;

a positional relation detecting means for obtaining in real time information regarding positional relations of the X-ray imaging system based on a current position of the X-ray imaging system and the external shape data of the three dimensional model;

an imaging system transport control means for controlling the X-ray imaging system transport mechanism in accordance with the information regarding the positional relations of the X-ray imaging system detected by the positional relation detecting means; and a top plate for carrying a subject being inspected, said top plate configured to move in reference to a common coordinate system of the X-ray imaging system having the mechanical center of the device as the reference point, wherein said shape data registering means further registers shapes of three dimensional models corresponding to the top plate's external shape; and said positional relation detecting means obtains the information regarding positional relations between the X-ray imaging system and the top plate based on their current positions and the external shape data of the three dimensional model so that the imaging system transport control means can control the X-ray imaging system transport mechanism in accordance with the information regarding the positional relation between the top plate and the X-ray imaging system.

20. A radiographic X-ray device comprising:

a plurality of X-ray imaging systems each comprising an X-ray tube for radiating X-rays and an X-ray detector for detecting transmitted X-rays, which are arranged to face each other and are mounted on each end of a support arm;

an X-ray imaging system transport mechanism for transporting the X-ray imaging systems using a common coordinate system having a mechanical center of the device as a reference point;

a shape data registering means for each X-ray imaging system for advance registration of external shape data of three dimensional models corresponding to three dimensional shapes of the X-ray imaging systems, wherein the shape data is obtained in Standard Triangle Language format, converted into voxel format data, and then converted into Binary Separated Partition data;

a positional relation detecting means for obtaining in real time information regarding positional relations of the X-ray imaging systems based on a current position of each X-ray imaging system and the external shape data of the three dimensional model; and an imaging system transport control means for controlling the X-ray imaging system transport mechanism in accordance with the information regarding the positional relations of the X-ray imaging systems detected by the positional relation detecting means.

* * * * *